US005637619A

United States Patent [19]
Sartorelli et al.

[11] Patent Number: 5,637,619
[45] Date of Patent: Jun. 10, 1997

[54] ANTITUMOR 2-AMINOCARBONYL-1, 2-BIS (METHYLSULFONYL)-1-(SUBSTITUTED) HYDRAZINES

[75] Inventors: Alan C. Sartorelli, Woodbridge; Krishnamurthy Shyam; Philip G. Penketh, both of Hamden, all of Conn.

[73] Assignee: Yale University, New Haven, Conn.

[21] Appl. No.: 497,931

[22] Filed: Jul. 5, 1995

[51] Int. Cl.⁶ .......................... A61K 31/175; A61K 31/22
[52] U.S. Cl. ...................... 514/590; 514/550; 514/601; 560/150; 564/35; 564/81
[58] Field of Search ................... 514/550, 601, 514/590; 564/81, 35; 560/150

[56] References Cited

U.S. PATENT DOCUMENTS

| 4,175,200 | 11/1979 | Hunter et al. | 564/35 |
| 4,684,747 | 8/1987 | Sartorelli et al. | 564/81 |
| 4,849,563 | 7/1989 | Sartorelli et al. | 514/155 |
| 5,101,072 | 3/1992 | Sartorelli et al. | 564/81 |
| 5,214,068 | 5/1993 | Sartorelli et al. | 514/601 |
| 5,256,820 | 10/1993 | Sartorelli et al. | 564/81 |

OTHER PUBLICATIONS

Shyam et al "Synthesis and Evaluation of N,N'–Bis(arylsulfonyl)hydrazines . . . " J. Med. Chem. v 28, p 525 (1985).
Hrubiec et al "Synthesis and Evaluation . . . " J. Med. Chem. v29 p 1777 (1986).
Shyam et al. "1,2–Bis(arylsulfonyl)hydrazines 2." J. Med. Chem. v29 p 1323 (1986).
Hrubiec et al "Synthesis and Evaluation . . . " J. Med. Chem. v29 p 1299 (1986).
Shyam et al "1,2–Bis(sulfonyl)hydrazines 3" J. Med. Chem. v30 p 2157 (1987).
Shyam et al. "Synthesis and Evaluation . . . " J. Med. Chem. v33 p 2259 (1990).
Shyam et al "Synthesis and Evaluation . . . " J. Med. Chem. v36 p 3496 (1993).
Penketh et al "Studies on the Mechanism . . . " J. Med. Chem. v37 p 2912 (1994).

*Primary Examiner*—Peter O'Sullivan
*Attorney, Agent, or Firm*—Henry D. Coleman; R. Neil Sudol

[57] ABSTRACT

The present invention relates to novel 2-aminocarbonyl-1, 2-bis(methylsulfonyl)-1-(2-chloroethyl)hydrazines and 2-aminocarbonyl-1,2-bis(methylsulfonyl)-1-methylhydrazines, and their use to treat malignant tumors. The agents are especially useful in the treatment of animal and human cancers. Two preferred agents in this class, especially for use in the treatment of tumors are 1,2-bis (methylsulfonyl)-1-(2-chloroethyl)-2-(2-chloroethyl) aminocarbonylhydrazine and 1,2-bis(methylsulfonyl)-1-(2-chloroethyl)-2-methylaminocarbonylhydrazine. These agents are characterized by the following: they are incapable of undergoing inactivation by the denitrosation mechanism proposed for the inactivation of the CNUs; they are incapable of generating a hydroxyethylating species by the mechanism proposed for the CNUs; and they are capable of chloroethylation or methylation and carbamoylation.

19 Claims, No Drawings

ANTITUMOR 2-AMINOCARBONYL-1, 2-BIS (METHYLSULFONYL)-1-(SUBSTITUTED) HYDRAZINES

This invention was made with government support under grant number CA-53340 awarded by the Department of Health and Human Services.

FIELD OF THE INVENTION

The present invention relates to 2-aminocarbonyl-1,2-bis (methylsulfonyl)-1-(substituted)hydrazines exhibiting antitumor activity in mammals. Methods of treating neoplasia, especially including solid tumors are additional aspects of the present invention.

BACKGROUND OF THE INVENTION

The search for compounds exhibiting enhanced antineoplastic activity has focused some attention on nitrosourea compounds such as 1,3-bis(2-chloroethyl)-1-nitrosourea (BCNU) and related agents. Several N-(2-chloroethyl)-N-nitrosoureas (CNUs) have been evaluated clinically and have been shown to possess significant antineoplastic activity against brain tumors, colon cancer and lymphomas (See, DeVita, et al., *Cancer Res.* 1965, 25, 1876–1881; Nissen, et al., *Cancer* 1979, 43, 31–40). Characterization of the decomposition products of the clinically used CNUs, such as BCNU and 1-(2-chloroethyl)-3-cyclohexyl-1-nitrosourea (CCNU), has resulted in the identification of several reactive products, including chloroethylating, carbamoylating and hydroxyethylating species (See, for example, Montgomery, et al., *J. Med. Chem.* 1967, 10, 668–674; Montgomery, et al., *J. Med. Chem.* 1975, 18, 568–571; Weinkam and Lin, *J. Med. Chem.* 1979, 22, 1193–1198; and Brundrett, R. B., *J. Med. Chem.* 1980, 23, 1245–1247).

The antitumor activity of the CNUs has been suggested to result from chloroethylation and subsequent crosslinking of DNA (See Kohn, K. W. in *Recent Results in Cancer Research* (Eds. Carter, S. K., Sakurai, Y., and Umezawa, H.), vol. 76, p. 141, Springer, Berlin (1981)). In support of this view is the observation that many chloroethylating agents with no carbamoylating activity (e.g., clomesone, as discussed by Shealy, et al., *J. Med. Chem.* 1984, 27, 664–670) possess excellent antineoplastic activity. In addition, replacement of the chloro group in CNUs by a hydroxyl group has resulted in a considerable decrease in antineoplastic activity (Montgomery, J. A., personal communication; cited by Gibson, et al., *Cancer Res.* 1986, 46, 553–557). Furthermore, there is some evidence that hydroxyethylation of DNA is a carcinogenic and/or mutagenic event (Pelfrene, et al., *J. Natl. Cancer Inst.* 1976, 56, 445–446; and Swenson, et al., *J. Natl. Cancer Inst.* 1979, 63, 1469–1473).

While hydroxyethylation seems to have no salutary effect on the antineoplastic activity of the CNUs, there appears to be some uncertainty regarding the role played by the carbamoylating species (i.e., the isocyanate). The isocyanate generated from the CNUs reacts with thiol and amine functionalities on proteins and inhibits DNA polymerase (Baril, et al., *Cancer Res.* 1975, 35, 1–5.), the repair of DNA strand breaks (Kann, et al., *Cancer Res.* 1974, 34, 398–402), and RNA synthesis and processing (Kann, et al., *Cancer Res.* 1974, 34, 1982–1988). In addition, BCNU has been shown to inhibit glutathione reductase, ribonucleotide reductase and thioredoxin reductase (Schallreuter, et al., *Biochim. Biophys. Acta* 1990, 1054, 14–20). Although it is believed by many that some of these same properties contribute to the toxic side effects of CNUs (Colvin, et al., *Biochem. Pharmacol.* 1976, 25, 695–699; Wheeler, et al., *Cancer Res.* 1974, 34, 194–200; and Panasci, et al., *Cancer Res.* 1977, 37, 2615–2618), it is entirely possible, as speculated by Gibson and Hickman (Gibson and Hickman, *Biochem. Pharmacol.* 1982, 31, 2795–2800) in their study of the effects of BCNU on the TLX tumor in mice, that intracellular release of isocyanates plays a role in modulating the biological activity of the CNUs against some specific tumor types. Caracemide, an investigational antitumor agent developed by the Dow Chemical Company (Newman and Farquhar, *Invest. New Drugs* 1987, 5, 267–271 and Slatter, et al., *Chem. Res. Toxicol.* 1993, 6, 335–340) is thought to act as a latent form of methyl isocyanate. This agent was shown to be active in a number of National Cancer Institute tumor models, including the mammary MX-1 and colon CX-1 human tumor xenografts implanted in the subrenal capsules of athymic mice (Clinical brochure "Caracemide NSC 253272", Division of Cancer Treatment, National Cancer Institute, 1983).

The hydroxyethylating species generated from the CNUs, 2-hydroxyethyldiazohydroxide, is thought to be formed from 4,5-dihydro-1,2,3-oxadiazole which, in turn, has been hypothesized to be the result of an internal cyclization reaction involving the N-nitroso group (Brundrett, R. B., *J. Med. Chem.* 1980, 23, 1245–1247). The N-nitroso group is also involved in the enzymatic inactivation of the CNUs. For example, BCNU can be inactivated by denitrosation by liver microsomal enzymes in an NADPH-dependent reaction, with the formation of 1,3-bis(2-chloroethyl)urea (Hill, et al., *Cancer Res.* 1975, 35, 296–301 and Lin and Weinkam, *J. Med. Chem.* 1981, 24, 761–763). The denitrosation reaction is catalyzed by NADPH:cytochrome P450 reductase in the case of CCNU (Potter and Reed, *Arch. Biochem. Biophys.* 1982, 216, 158–169 and Potter and Reed, *J. Biol. Chem.* 1983, 258, 6906–6911). BCNU has also been shown to undergo glutathione-dependent denitrosation catalyzed by rat (Smith, et al., *Cancer Res.* 1989, 49, 2621–2625) and human (Berhane, et al., *Cancer Res.* 1993, 53, 4257–4261) glutathione S-transferase mu isoenzymes.

Since tumor cell-catalyzed denitrosation could conceivably be a potential mechanism of resistance to the CNUs, our aim was to synthesize a series of compounds that (a) were capable of generating a chloroethylating or methylating species; (b) were capable of forming a carbamoylating species; (c) were devoid of hydroxyethylating activity; and (d) were free from structural features that would make them highly prone to metabolic inactivation.

We believed that 2-aminocarbonyl-1,2-bis (methylsulfonyl)-1-(substituted)hydrazines (I) might satisfy the above conditions for the following reasons:

(a) Base-catalyzed elimination of compounds I would result in the formation of a chloroethylating or methylating species and a carbamoylating agent as shown below.

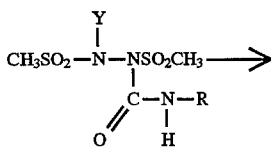

I

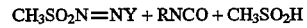

II

3
-continued (Y is Methyl or 2-Chloroethyl)

(b) At least three classes of prodrugs of species II, i.e., 1,2-bis(methylsulfonyl)-1-(2-chloroethyl)hydrazine, 1-(2-chloroethyl)-1,2,2-tris(methylsulfonyl)hydrazine (Shyam, et al., *J. Med. Chem.* 1990, 33, 2259–2264), and 1-acyl-1,2-bis(methylsulfonyl)-2-(2-chloroethyl) hydrazine (Shyam, et al., *J. Med. Chem.* 1993, 36, 3496–3502), with potent antitumor activity, have been identified.

(c) The formation of a 4,5-dihydro-1,2,3-oxadiazole intermediate may be prevented by the absence of an N-nitroso moiety. This, in turn, may prevent the formation of a 2-hydroxyethylating agent. The absence of an N-nitroso group may also make the compounds less prone to metabolic inactivation.

OBJECTS OF THE INVENTION

It is an object of the invention to provide effective antineoplastic agents effective for treating numerous cancerous conditions, including solid tumors in animals and humans.

It is another object of the invention to provide antineoplastic agents which are capable of generating a carbamoylating and chloroethylating chemical species.

It is yet a further object of the invention to provide effective antineoplastic agents which are less prone to metabolic inactivation than compounds of related structure.

It is an additional object of the invention to provide pharmaceutical compositions based upon the use of these novel antineoplastic agents.

It is still another object of the invention to provide methods of treating neoplasia, including solid tumors, in animals and humans.

These and/or other objects of the invention may be readily gleaned from the description of the invention which follows.

SUMMARY OF THE INVENTION

The present invention relates to 2-aminocarbonyl-1,2-bis (methylsulfonyl)-1-(substituted)hydrazine compounds of the formula:

where

Y is —CH$_3$ or —CH$_2$CH$_2$Cl, and

R is C$_1$–C$_7$ alkyl, cyclohexyl, methylcyclohexyl, —CH$_2$CH=CH$_2$, —CH$_2$CH$_2$Cl, —CH$_2$CH$_2$CH$_2$Cl, —CH$_2$COOC$_2$H$_5$, —CH(CH$_3$)COOC$_2$H$_5$ or —CH (CH$_2$C$_6$H$_5$)COOC$_2$H$_5$.

In preferred compounds according to the present invention, Y is —CH$_2$CH$_2$Cl and R is —CH$_2$CH$_2$Cl, —CH$_2$CH=CH$_2$ or —CH$_3$. R is most preferably —CH$_2$CH$_2$Cl or —CH$_3$. The C$_1$–C$_7$ alkyl substituent is preferably selected from the group consisting of methyl, ethyl, n-propyl, isopropyl, n-butyl, isobutyl, t-butyl, n-pentyl, isopentyl, n-hexyl, isohexyl and substituted hexyl. The compounds according to the present invention are produced by synthetic methods which are readily known to those of ordinary skill in the art and include the disclosed chemical synthetic methods.

The present invention also relates to pharmaceutical compositions comprising an antineoplastic effective amount of a 2-aminocarbonyl-1,2-bis(methylsulfonyl)-1-(substituted) hydrazine compound as set forth above. These pharmaceutical compositions preferably also include a pharmaceutically acceptable additive, carrier or excipient.

The present invention also relates to a method for treating neoplasia in mammals comprising administering an antineoplastic effective amount of 2-aminocarbonyl-1,2-bis (methylsulfonyl)-1-(substituted)hydrazine compound to a patient suffering from cancer. The treatment of solid malignant tumors comprising administering to a patient an antitumor effective amount of one or more of these agents is a preferred embodiment of the present invention. The treatment of leukemias, lung carcinomas, melanoma, reticulum cell sarcoma, among various other related disease states may also be effected using the compounds of the present invention.

DETAILED DESCRIPTION OF THE INVENTION

The term "neoplasia" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors.

The term antineoplastic effective amount is used throughout the specification to describe an amount of the present compounds which is used to treat a patient suffering from a cancerous tumor to prevent the further growth of the neoplasms, bring that growth under control and preferably, produce a remission of the tumor.

The term "therapeutically effective amount" is used throughout the specification to describe that amount of the compound according to the present invention which is administered to a mammalian patient, especially including a human patient, suffering from cancer, to reduce or inhibit the growth or spread of the hematogenous, ascitic or solid tumor. Preferably, the compounds according to the present invention will result in a remission of the malignant hematogenous, ascitic or solid tumor. In the case of solid tumors, the compounds according to the present invention will inhibit the further growth of the tumor tissue and shrink the existing tumor.

The present invention is directed to 2-aminocarbonyl-1, 2-bis(methylsulfonyl)-1-(substituted)hydrazine compounds of the formula:

where

Y is —CH$_3$ or —CH$_2$CH$_2$Cl; and

R is C$_1$–C$_7$ alkyl, cyclohexyl, methylcyclohexyl, —CH$_2$CH=CH$_2$, —CH$_2$CH$_2$Cl, —CH$_2$CH$_2$CH$_2$Cl, —CH$_2$COOC$_2$H$_5$, —CH(CH$_3$)COOC$_2$H$_5$ or —CH (CH$_2$C$_6$H$_5$)COOC$_2$H$_5$.

In preferred compounds according to the present invention, Y is —CH$_2$CH$_2$Cl and R is —CH$_2$CH$_2$Cl, —CH$_2$CH=CH$_2$, or —CH$_3$. R is most preferably —$CH_2CH_2Cl$ or —$CH_3$. Where R is $C_1$-$C_7$ alkyl, R is selected from the group consisting of methyl, ethyl, n-propyl, isopropyl, n-butyl, isobutyl, t-butyl, n-pentyl, isopentyl, n-hexyl, isohexyl or substituted hexyl.

These compounds, which contain a 2-aminocarbonyl group, exhibit enhanced activity against a broad spectrum of neoplastic disease states, including, for example, numerous solid tumors. In in vivo screening tests, these agents have exhibited broad spectrum activity against a wide range of neoplastic disease states. In one case, where R is $CH_2CH_2Cl$, this compound exhibited unexpectedly greater antineoplastic activity than mitomycin C or cyclophosphamide, among the most effective commercial antineoplastic alkylating agents.

The present compounds represent prodrug forms of intermediates which are believed to exhibit their activity through chloroethylation, methylation and/or carbamoylation mechanisms.

The compounds according to the present invention are primarily useful for their antineoplastic activity, including their activity against solid tumors. In addition, these compositions may also find use as intermediates in the chemical synthesis of other useful antineoplastic agents which are, in turn, useful as therapeutic agents or for other purposes.

Compounds according to the present invention are synthesized by the adaptation of techniques which are well known in the art. 2-Aminocarbonyl-1,2-bis(methylsulfonyl)-1-(substituted)hydrazines (I, Y is —$CH_3$ or —$CH_2CH_2Cl$) are synthesized by reacting 1,2-bis(methylsulfonyl)-1-methylhydrazine or 1,2-bis(methylsulfonyl)-1-(2-chloroethyl)hydrazine with the appropriate isocyanate (where R is of the indicated structure or a related alkyl structure) in dry acetonitrile in the presence of triethylamine as shown below. The synthesis of the appropriate isocyanate derivative for use in this reaction scheme is well known in the art and uses standard chemical techniques.

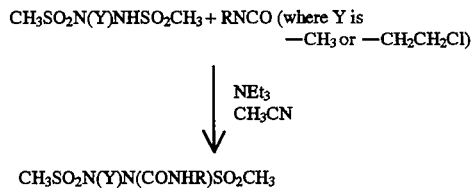

III. R=—$CH_2CH_2Cl$
IV. R=—$CH_3$
V. R=—$CH_2CH=CH_2$
VI. R=—$CH_2CH_2CH_2Cl$
VII. R=—$CH_2COOC_2H_5$
VIII. R=—$CH(CH_3)COOC_2H_5$
IX. R=—$CH(CH_2C_6H_5)COOC_2H_5$
X. R=—$C_2$-$C_7$ alkyl, cyclohexyl or methylcyclohexyl After synthesis, the residue generally is triturated, washed with dilute acid, dried, triturated again and recrystallized from an appropriate solvent, for example, ethanol or ethanol/petroleum ether. Modification of the disclosed chemical synthetic methods may be readily made by those of ordinary skill in the art in order to provide alternative synthetic pathways to the present compounds.

The present invention also relates to pharmaceutical compositions comprising a therapeutically effective amount of a 2-aminocarbonyl-1,2-bis(methylsulfonyl)-1-(substituted) hydrazine compound as set forth above. A therapeutically effective amount of one or more of these compounds is that amount which may be used to treat patients suffering from cancer such as a malignant tumor. These pharmaceutical compositions preferably also include a pharmaceutically acceptable additive, carrier or excipient. In pharmaceutical compositions according to the present invention which relate to the treatment of malignant solid tumors, those compositions comprise an amount of one or more 2-aminocarbonyl-1,2-bis(methylsulfonyl)-1-(substituted)hydrazine compounds as set forth above effective to inhibit the growth of the treated tumor and, in certain cases, to actually shrink the treated tumor.

One of ordinary skill in the art will recognize that a therapeutically effective amount of the compounds according to the present invention to be used to treat malignant tumors will vary with the disease state or condition to be treated, its severity, the treatment regimen to be employed, the result desired (remission, shrinkage of tumor in combination with surgical techniques or radiation), the type of administration used to deliver the compounds, the pharmacokinetics of the compounds used, as well as the patient (animal or human) treated.

In the pharmaceutical aspect according to the present invention, one or more compounds according to the present invention is formulated preferably in admixture with a pharmaceutically acceptable additive, carrier or excipient. In general, it is preferable to administer the pharmaceutical composition in parenteral-administrable form (preferably, intravenous), but consideration should be given to other formulations administered via intramuscular, transdermal, buccal, subcutaneous, suppository, oral or other route. Of course, one of ordinary skill in the art may modify the formulations within the teachings of the specification to provide numerous formulations for a particular route of administration without rendering the compositions of the present invention unstable or compromising the therapeutic activity.

For example, modifying the present compounds to render them more soluble in water or other vehicle, for example, may be easily accomplished by minor modifications (salt formulation, esterification, etc.) which are well within the ordinary skill in the art. It is also within ordinary skill to modify the route of administration and dosage regimen of a particular compound in order to manage the pharmacokinetics of the present compounds for maximum beneficial effect in the patient to be treated. Sustained and/or controlled release forms of the pharmaceutical compositions are also contemplated by the present invention.

The present compounds are prodrug forms of reactive intermediates. In certain pharmaceutical dosage forms, the present compounds may be modified to other prodrug forms to take advantage of a particular route of administration of the active compounds. One of ordinary skill in the art will recognize how to readily modify the present compounds to alternative prodrug forms to facilitate delivery of active compounds to a targeted site within the patient. The individual of ordinary skill also will take advantage of favorable pharmacokinetic parameters of the prodrug forms, where applicable, in delivering the present compounds to a targeted site within the patient to maximize the intended antineoplastic effect of the compound.

The amount of compound included within the therapeutically active formulations according to the present invention is an effective amount for treating the malignant tumor. In general, a therapeutically effective amount of the compound according to the present invention in dosage form usually ranges from less than about 0.05 mg/kg to about 500 mg/kg of body weight of the patient to be treated, or considerably more, depending upon the compound used, the tumor type to be treated, the ability of the active compound to localize in the tissue to be treated, the route of administration and the pharmacokinetics of the compound in the patient. In the case of treating solid tumors, the compound is preferably administered in amounts ranging from about 0.05 mg/kg to about 250 mg/kg or more at one time. This dosage range generally produces effective blood level concentrations of active compound ranging from about 0.01 to about 500 micrograms per ml of blood in the patient to be treated. The duration of treatment may be for one or more days or may last for several months or considerably longer (years) depending upon the disease state treated.

Administration of the active compound may range from continuous (intravenous drip) to intramuscular, to several oral administrations per day (for example, Q.I.D.) and may include parenteral, including intravenous and intramuscular, oral, topical, subcutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., parenteral or oral.

For parenteral formulations, the carrier may comprise sterile water or aqueous sodium chloride solution in combination with other ingredients which aid dispersion, such as ethanol and other pharmaceutically acceptable solvents, including DMSO, among others. Of course, where solutions are to be used and maintained as sterile, the compositions and carriers must also be sterilized. Injectable suspensions may also be prepared, in which case appropriate liquid carriers, suspending agents and the like may be employed.

In preparing pharmaceutical compositions in oral dosage form, any one or more of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric coated or sustained release by standard techniques.

The compounds and compositions according to the present invention are used to treat cancer in mammals, including humans. Generally, to treat malignant tumors, the compositions will be administered in parenteral, preferably intravenous dosage form in amounts ranging from about 25 micrograms up to about 500 mg or more one to four times per day. The present compounds are preferably administered parenterally, but they also may be administered in an alternative manner, for example, orally or even topically or in suppository form.

Compounds according to the present invention may be administered alone or in combination with other agents, especially including other compounds of the present invention. In addition, the administration of one or more compounds according to the present invention with other antineoplastic agents, in combination chemotherapy, such as antimetabolites, etoposide, doxorubicin, taxol, vincristine, cyclophosphamide or mitomycin C, among numerous others, is contemplated by the present invention.

While not being limited by way of theory, it is believed that the compounds according to the present invention primarily induce their therapeutic effect in treating malignant tumors by functioning as combined chloroethylating and carbamoylating agents, without also providing hydroxyethylating activity.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Experimental Section

Synthesis. Melting points were determined in capillary tubes on a Thomas-Hoover melting point apparatus and are uncorrected. $^1$H NMR spectra were recorded on a Varian EM-390 spectrometer with tetramethyl silane as an internal standard. Elemental analyses were performed by the Baron Consulting Co., Orange, Conn. and the data were within±0.4% of the theoretical values for the 2-aminocarbonyl-1,2-bis(methylsulfonyl)-1-(2-chloroethyl) hydrazines.

Example 1

Synthesis of 1,2-bis(methylsulfonyl)-1-(2-chloroethyl)-2-(2-chloroethyl) aminocarbonylhydrazine (III)

To a stirred solution of 1,2-bis(methylsulfonyl)-1-(2-chloroethyl)hydrazine (Shyam, et al.,*J. Med. Chem.*, 1990, 33, 2259–2264) (2.5 g, 0.010 mol) and 2-chloroethyl isocyanate (1.2 g, 0.011 mol) in dry acetonitrile (100 mL) was added triethylamine (1.1 g, 0.011 mol) at room temperature. After an additional 10 min, the reaction mixture was evaporated to dryness in vacuo. The residue was triturated twice with 15 mL quantities of petroleum ether and the petroleum ether layer was discarded each time. The residue was then taken up in ethyl acetate (150 mL) and washed with dilute hydrochloric acid (3×15 mL). The ethyl acetate layer was dried over anhydrous magnesium sulfate and filtered. Upon evaporation of the solvent, a semi-solid residue was obtained which, upon trituration with absolute ethanol, gave a white solid. Recrystallization from ethanol afforded 1.5 g (42.2%) of the title compound: mp 96°–97.5° C.; $^1$H NMR (acetone-d6) δ 7.0 (br, 1 H, NH), 3.7–4.2 (m, 4 H, SO$_2$NCH$_2$CH$_2$Cl ), 3.5–3.7 (m, 4H, CONHCH$_2$CH$_2$Cl), 3.5 and 3.3 (2s, 6 H, 2 CH$_3$). Anal. (C$_7$H$_{15}$C$_{12}$N$_3$O$_5$S$_2$) C, H, N.

Examples 2–7

SYNTHESIS OF 2-AMINOCARBONYL-1,2-BIS (METHYLSULFONYL)-1-(2-CHLOROETHYL) HYDRAZINES

The following compounds were prepared using procedures similar to the one described in example 1 for compound III.

1,2-Bis(methylsulfonyl)-1-(2-chloroethyl)-2-methylaminocarbonylhydrazine (IV) was synthesized according to the method of example 1. Compound IV was recrystallized from ethanol: yield 42.4%; mp 146°–147.5° C.; $^1$H NMR (acetone-d6) δ 6.7 (br, 1 H, NH), 3.7–4.2 (m, 4 H, CH$_2$CH$_2$Cl ), 3.5 and 3.3 (2 s, 6 H, 2 CH$_3$), 2.9 (d, 3 H, NCH$_3$). Anal. (C$_6$H$_{14}$ClN$_3$O$_5$S$_2$) C, H, N.

2-Allylaminocarbonyl-1,2-bis(methylsulfonyl)-1-(2-chloroethyl)hydrazine (V) was synthesized according to the method of example 1. Compound V was recrystallized from ethanol: yield 42.2%; mp 105°–106° C.; $^1$H NMR (acetone-d6) δ 6.9 (br, 1 H, NH), 5.6–6.1 (m, 1 H, CH=C), 5.4, 5.2 and 5.1 (3 d, 2H, C=CH$_2$), 3.7–4.2 (m, 6 H, NHCH$_2$ and CH$_2$CH$_2$Cl), 3.5 and 3.3 (2 s, 6 H, 2 CH$_3$). Anal. (C$_8$H$_{16}$ClN$_3$O$_5$S$_2$) C, H, N.

1,2-Bis(methylsulfonyl)-1-(2-chloroethyl)-2-(3-chloropropyl)aminocarbonylhydrazine (VI) was synthesized according to the method of example 1. Compound VI was recrystallized from ethanol: yield 35.2%; mp 85°–86° C.; $^1$H NMR (acetone-d6) δ 6.8 (br, 1 H, NH), 3.7–4.2 (m, 4 H, SO$_2$NCH$_2$CH$_2$Cl), 3.4–3.8 (m, 6 H, CH$_2$CH$_2$CH$_2$Cl), 3.5 and 3.3 (2 s, 6 H, 2 CH$_3$). Anal. (C$_8$H$_{17}$Cl$_2$N$_3$O$_5$S$_2$) C, H, N.

1,2-Bis(methylsulfonyl)-1-(2-chloroethyl)-2-(ethoxycarbonylmethyl)aminocarbonylhydrazine (VII) was synthesized according to the method of example 1. Compound VII was recrystallized from ethanol: yield 42.2%; mp 121°–122° C.; $^1$H NMR (acetone-d6) δ 7.1 (br, 1 H, NH), 3.7–4.4 (m, 8 H, OCH$_2$, NHCH$_2$ and CH$_2$CH$_2$Cl), 3.5 and 3.3 (2 s, 6 H, 2 CH$_3$), 1.2 (t, 3 H, CCH$_3$). Anal. (C$_9$H$_{18}$ClN$_3$O$_7$S$_2$) C, H, N.

1,2-Bis(methylsulfonyl)-1-(2-chloroethyl)-2-(1-ethoxycarbonylethyl)aminocarbonylhydrazine (VIII) was synthesized according to the method of example 1. Compound VIII was recrystallized from ethanol: yield 28.0%; mp 111°–112° C.; $^1$H NMR (acetone-d6) δ 6.9 (br, 1 H, NH), 3.7–4.6 (m, 7 H, OCH$_2$, NHCH and CH$_2$CH$_2$Cl), 3.5 and 3.3 (2 s, 6 H, 2 CH$_3$), 1.4 (d, 3 H, CHCH$_3$), 1.2 (t, 3 H, CH$_2$CH$_3$). Anal. (C$_{10}$H$_{20}$ClN$_3$O$_7$S$_2$) C, H, N.

1,2-Bis(methylsulfonyl)-1-(2-chloroethyl)-2-(1-ethoxycarbonyl-2-phenylethyl)aminocarbonylhydrazine (IX) was synthesized according to the method of example 1. Compound IX was recrystallized from ethanol-petroleum ether: yield 12.8%; mp 106°–107° C.; $^1$H NMR (acetone-d6) δ 7.1–7.3 (m, 5 H, C$_6$H$_5$), 6.8 (br, 1 H, NH), 4.6 (m, 1 H, NHCH), 3.6–4.3 (m, 6 H, OCH$_2$ and CH$_2$CH$_2$Cl), 3.5 (s, 3 H, CH$_3$SO$_2$), 3.0–3.3 (s, m, 5 H, CH$_2$C$_6$H$_5$, CH$_3$SO$_2$), 1.2 (t, 3 H, CH$_2$CH$_3$). Anal. (C$_{16}$H$_{24}$ClN$_3$O$_7$S$_2$) C, H, N.

2-Aminocarbonyl-1,2-bis(methylsulfonyl)-1-methylhydrazine methylhydrazine compounds containing the same aminocarbonyl substituents are prepared by analogy by following the synthetic protocols described above.

Example 8

Antitumor Activity

Antitumor Activity was tested in several cell lines: L1210 leukemia, B16F10 melanoma, M5076 reticulum cell sarcoma, M109 lung carcinoma and LX-1 lung carcinoma.

Leukemia L1210 Testing

Leukemia L1210 cells were obtained from the Frederick Cancer Research Facility, Division of Cancer Treatment Tumor Repository of the National Cancer Institute, and were maintained by serial passage in tissue culture. Every 8 weeks, tumor cells were injected intraperitoneally into five donor CD$_2$F$_1$ mice 8- to 10- weeks of age and were allowed to grow for 7 days. The peritoneal fluid was withdrawn and the suspension was centrifuged for 5 min at 1600 g. The supernatant was decanted and 10$^5$ cells/mL were seeded into 10 mL of RPMI 1640 medium supplemented with 10% fetal bovine serum and 1% L-glutamine, and once again maintained in culture. To assay for antineoplastic activity, 0.1 mL of the cell suspension containing 10$^5$ L1210 leukemia cells was injected ip into each recipient mouse. Test compounds were administered over a wide range of dosage levels, beginning 24 h after tumor implantation, and continued once daily for 6 consecutive days. All drugs were administered ip as a solution in 100% dimethylsulfoxide (DMSO), in a volume not exceeding 0.025 mL. In each experiment, animals were distributed into groups of five mice of comparable weight and maintained throughout the course of the experiment on Purina Laboratory Chow pellets and water adlibitum. Control tumor-bearing animals given comparable volumes of vehicle were included in each experiment. Mice were weighed during the course of the experiments, and the percentage change in body weight from onset to termination of therapy was used as an indication of drug toxicity. Determination of the sensitivity of neoplasms to these agents was based upon the prolongation of survival time afforded by the drug treatments.

Results of L1210 Testing

The tumor-inhibitory properties of compounds III-IX were determined in initial tests by measuring their effects on the survival time of mice bearing the intraperitoneally (ip) implanted L1210 leukemia; the results of these tests are summarized in Table 1, below. With the exception of compound VI, all of the agents synthesized produced "cures" (defined as tumor-free 60 days post-tumor implant) in 100% of mice bearing the L1210 leukemia at one or more of the dosage levels examined following ip administration. It is conceivable that compound VI failed to do so only because it was not evaluated at daily dosage levels greater than 15 mg/kg given for 6 consecutive days. Compound VI did, however, produce a partial cure rate of tumor-bearing mice at the highest dosage level examined. Compounds III and IV appeared to have much better therapeutic potential than the amino acid ester derivatives, i.e., compounds VII, VIII and IX. Thus, the methyl urea derivative (IV) produced a 40% cure rate of tumor-bearing mice at 5 mg/kg administered for 6 consecutive days with no body weight loss. This agent also cured 100% of mice bearing the L1210 leukemia at 10 and 15 mg/kg×6 with less than a 6% loss of body weight. The 2-chloroethyl urea derivative (III), which can be regarded as a structural analog of BCNU, cured 80 to 100% of leukemic mice at 10 to 20 mg/kg×6, although at the highest dose examined, i.e., 20 mg/kg, it appeared to be somewhat toxic, as evidenced by a 10.4% loss in body weight. The allyl urea derivative (V) was also highly efficacious against this tumor, curing 100% of mice receiving a daily dosage of 15 mg/kg given for 6 consecutive days. The amino acid ester derivatives (VII-IX), in general, appeared to be considerably less potent than compounds III-V requiring daily dosage levels in the range of 25 to 100 mg/kg to achieve optimum cure rates, and early deaths of treated mice occurred at higher doses in each case.

TABLE 1

Effects of 2-Aminocarbonyl-1,2-bis(methylsulfonyl)-1-(2-chloroethyl)hydrazines On the Survival Time of Mice Bearing the L1210 Leukemia

| Compound | Daily Dose mg/kg$^a$ | Av.Wt. Change %$^b$ | %T/C$^c$ | % 60 Day Survivors |
|---|---|---|---|---|
| III | 10 | −4.7 | — | 100 |
|  | 15 | −4.0 | 216 | 80 |
|  | 20 | −10.4 | 239 | 80 |
| IV | 5 | +9.9 | 234 | 40 |
|  | 10 | −5.6 | — | 100 |
|  | 15 | −2.1 | — | 100 |
| V | 5 | −1.6 | 184 | 20 |
|  | 10 | −2.1 | 394 | 40 |

TABLE 1-continued

Effects of 2-Aminocarbonyl-1,2-bis(methylsulfonyl)-1-
(2-chloroethyl)hydrazines On the Survival Time of Mice
Bearing the L1210 Leukemia

| Compound | Daily Dose mg/kg[a] | Av.Wt. Change %[b] | %T/C[c] | % 60 Day Survivors |
|---|---|---|---|---|
|    | 15  | −2.9 | —   | 100 |
| VI | 5   | −2.8 | 111 | —   |
|    | 10  | −5.6 | 187 | —   |
|    | 15  | −8.8 | 192 | 20  |
| VII| 5   | −1.5 | 151 | —   |
|    | 10  | −1.4 | 202 | 20  |
|    | 15  | −0.5 | 202 | —   |
|    | 20  | −3.7 | 191 | 20  |
|    | 25  | −0.5 | —   | 100 |
|    | 50  | −2.5 | 138 | 80  |
|    | 75  | −1.5 | 119 | 60  |
|    | 100 | −4.0 | 115 | —   |
| VIII| 5  | −2.0 | 170 | —   |
|    | 10  | −1.4 | 178 | 20  |
|    | 15  | −0.5 | 185 | —   |
|    | 20  | −1.5 | 227 | —   |
|    | 25  | −2.5 | 239 | 60  |
|    | 50  | −3.3 | —   | 100 |
|    | 75  | −2.5 | 125 | 80  |
|    | 100 | −2.5 | 118 | —   |
| IX | 5   | −2.5 | 147 | —   |
|    | 10  | −0.5 | 165 | —   |
|    | 15  | −1.9 | 160 | —   |
|    | 20  | −1.9 | 174 | —   |
|    | 25  | −0.9 | 177 | —   |
|    | 50  | −2.0 | 225 | 60  |
|    | 100 | −2.0 | —   | 100 |
|    | 150 | −5.0 | 169 | 20  |

[a]Administered ip once daily for six consecutive days, beginning 24 hours after tumor implantation, with 5–10 mice being used per group.
[b]Average percent change in body weight from onset to termination of therapy.
[c]%T/C = average survival time of treated/control mice × 100; cures (>60-day survivors) are listed separately and are not included in this calculation.

[a]Administered ip once daily for six consecutive days, beginning 24 hours after tumor implantation, with 5–10 mice being used per group. [b]Average percent change in body weight from onset to termination of therapy. [c]% T/C= average survival time of treated/control mice×100; cures (>60-day survivors) are listed separately and are not included in this calculation.

B16F10 Melanoma, M5076 Reticulum Cell Sarcoma, M109 Lung Carcinoma and LX-1 Lung Carcinoma Testing B16F10 melanoma cells were grown in vitro as monolayers in minimum essential medium with Hank's salts supplemented with 10% fetal bovine serum and 1% 200 mM L-glutamine solution. Solid tumors were produced in C57BL/6 female mice 12- to 14-weeks of age by the intradermal injection in the right flank of each mouse of 0.1 mL of a cell suspension containing $10^6$ B16F10 cells/mL from freshly trypsinized cultures. After 10–12 days, animals bearing approximately 100 mm$^3$ tumors were treated ip with compound III or IV dissolved in 100% DMSO for 6 consecutive days, and tumor volumes were measured on alternate days until reaching 1000 mm$^3$.

The M5076 reticulum cell sarcoma was passaged biweekly by sc transfer of tumor fragments into C57BL/6 mice, and the M109 lung carcinoma was similarly passaged in BALB/c mice. The LX-1 human lung carcinoma was passaged sc every two to three weeks in BALB/c-background athymic (nu/nu) mice. For use in these systems, compound III was dissolved in: (a) 100% DMSO and administered by iv injection in a fixed volume of 10 microliters; or (b) DMSO diluted with saline to a final concentration of 10% DMSO and administered iv in a volume of 0.01 milliliter/g of body weight. These different modes of formulation resulted in differences in the optimum effective dose found in the various tumor systems. Mitomycin C and cyclophosphamide were dissolved and administered in saline. BCNU and MeCCNU were dissolved in ethanol and diluted 1:9 (v/v) with water prior to administration.

Five mice per group were employed in experiments with the B16F10 melanoma, and 8 mice per group with the M5076 sarcoma, the M109 carcinoma and the LX-1 carcinoma. A minimum of two dose levels per compound were included in each evaluation and drug therapy was initiated 24 h after tumor implantation for the M5076 sarcoma and M109 carcinoma. In the LX-1 experiment, tumor bearing mice were selected and sorted into treatment and control groups on day 6 post-tumor implant such that all tumor weights ranged from 50–100 mg and median tumor weights per group were reasonably similar. Therapeutic results are presented in terms of: (a) increases in lifespan reflected by the relative median survival time (MST) of treated versus control groups (i.e., %T/C values), and by long-term survivors, and (b) primary tumor growth inhibition (i.e., T-C values) determined by calculating the relative median times for treated (T) and control untreated (C) mice to grow tumors of a 0.5 g size for the LX-1 carcinoma or a 1 g size for the murine neoplasms. Tumor weights were interchangeable with tumor size on the basis of 1 mm$^3$=1 mg. The activity criterion for increased lifespan was a T/C of ≧125%. The activity criterion for tumor inhibition was a delay in tumor growth consistent with one $\log_{10}$ cell kill (LCK). The absolute T-C value needed to attain this level of efficacy varied from experiment to experiment and depended upon the tumor volume doubling time of the control mice in each study. Treated mice dying prior to day 10 in the ip M109 experiment, or dying before their tumors achieved 0.5 g for the LX-1 carcinoma or 1 g in size for all other sc tumor models, were considered to have died from drug toxicity. Groups of mice with more than one death due to drug toxicity were not used in the evaluation of antitumor efficacy. Statistical evaluations of data were performed using Gehan's generalized Wilcoxan test (Gehan, *Biometrika*, 1965, 52, 203–233).

Results of B16F10 Melanoma, M5076 Reticulum Cell Sarcoma, M109 Lung Carcinoma and LX-1 Lung Carcinoma Testing One of the most active and potent compounds in the series as tested in the L1210 system as described above, compound III, was also evaluated against several other transplanted tumors (Table 2, below). When administered at the highest dose examined, i.e, three ip doses of 50 mg/kg given at 4 day intervals in the ip-implanted M109 lung carcinoma model, this compound produced a %T/C of 267. In the same system, but in a different experiment, the acetyl derivative (X) produced a comparable %T/C of 231 at the highest dosage level examined (60 mg/kg per injection), when the drug was administered ip using the same schedule (Shyam, et al., *J. Med. Chem.* 1993, 36, 3496–3502).

$CH_3SO_2N(CH_2CH_2Cl)N(COCH_3)SO_2CH_3$      X

TABLE 2

Summary of Optimal Antitumor Effects of 1,2-Bis(methylsulfonyl)-
1-(2-chloroethyl)-2-(2-chloroethyl)aminocarbonylhydrazine (III)
on
M109, M5076 and LX-1 Tumors

| Tumor, Site | Treatment Schedule, Route | Optimal Effective Dose, mg/kg/injection | %T/C, (Cures/Total), and/or [T-C, days] |
|---|---|---|---|
| M109, ip | q4d × 3; d.1[a]; ip | 50 [b,c] | 267 |
| M109, sc | q4d × 3; d.1[a]; iv | 50[c] | a)[d]115[8.3] |
|  | q3d × 4; d.1[a]; iv | 24[32][c,e] | b)[d]143[9.3] |
|  |  | 64[f] | b)[d]145[17.8] |
| M5076, sc | q2d × 5; d.1[a]; iv | 48[f] | >157(6/8) |
| LX-1, sc | q2d × 5; d.6[a]; iv | 40[f] | [14.5] |

[a]Day treatment initiated.
[b]Highest dose tested.
[c]Administered in 10% DMSO in saline.
[d]Each letter (a,b) signifies a different experiment.
[e]Dose in brackets producing the maximum T-C obtained.
[f]Administered in 100% DMSO.

Compound III was also evaluated against the M109 lung carcinoma implanted subcutaneously (sc). In the initial test using this model, a dose of 50 mg/kg per injection of this compound was administered intravenously (iv) in 10% DMSO in saline every fourth day for a total of three injections. While the maximum %T/C achieved (115) was not considered to be an active result, a meaningful delay in tumor growth (T-C) of 8.3 days was observed under these conditions. Mitomycin C, used as a reference drug, produced a maximum %T/C of 103 and a delay in tumor growth of 10 days (data not shown). A subsequent evaluation of compound III was performed using four different doses on a slightly different schedule, i.e., 24, 32, 48 and 64 mg/kg administered every third day for four total injections, and two vehicles, 10% DMSO in saline and 100% DMSO. When administered in 10% DMSO in saline, compound III produced a maximum %T/C of 143 and a maximum delay in tumor growth of 9.3 days at 24 and 32 mg/kg per injection, respectively; the next higher dose evaluated, 48 mg/kg per injection, was excessively lethal. At the highest level evaluated, 64 mg/kg per injection, made possible by the use of 100% DMSO as the vehicle, compound III achieved a maximum %T/C of 145 and a delay in tumor growth of 17.8 days, without causing any treatment-associated lethalities. The latter antitumor effect was statistically superior (p<0.01) to the best T-C value achieved with this compound in 10% DMSO in saline. Cyclophosphamide and mitomycin C were included as reference drugs in the last experiment. The former compound produced a maximum %T/C of 143 and a delay in tumor growth of 8.8 days, while mitomycin C produced a maximum %T/C of 134 and a T-C value of 9.3 days (data not shown). As reported earlier, compound X achieved a maximum %T/C of 136 and a maximum T-C value of 14.5 days against this tumor (Shyam, et al., *J. Med. Chem.*, 1993, 36, 3496).

Compound III was also evaluated against the M5076 reticulum cell sarcoma implanted sc. When administered iv at a level of 48 mg/kg per injection in 100% DMSO every other day for five days, compound III cured 6 out of 8 mice and consequently, no median time (T-C value) to reach 1 gram size tumors was expressed for this group. Tumor growth in mice receiving only 100% DMSO was indistinguishable from that of untreated control animals. 1-(2-Chloroethyl)-3-(4-methylcyclohexyl)-1-nitrosourea (MeCCNU) and BCNU were included in this experiment for comparison. The former achieved a maximum %T/C of 128 and a delay in tumor growth of 33.5 days at 16 mg/kg per injection administered iv every fourth day for three total injections, while BCNU, administered iv on the same treatment schedule, produced a %T/C in excess of 157, with 2 out of 8 cures, and a T-C of >62 days (data not shown). Since compound X, a chloroethylating agent with no carbamoylating activity, is much less active than compound III or BCNU against this tumor, it seems probable that the generation of an isocyanate intermediate contributes to the antineoplastic properties of chloroethylating agents against the M5076 sarcoma.

The human lung tumor, LX-1, xenografted sc in athymic mice, was also used to examine the antineoplastic potential of compound III. Treatment was initiated on day 6 post-implant when the median weight of the tumors was approximately 100 mg. A dose of 40 mg/kg per injection of compound III administered iv in 100% DMSO on an every other day schedule for a total of five injections was optimal; this regimen produced a median delay of 14.5 days in the growth of this tumor to a target size of 0.5 g. This level of activity, 1.6 LCK, compared favorably with that obtained with BCNU in the same experiment, which produced a T-C of 11.8 days (1.3 LCK) at the optimum dosage of 20 mg/kg per injection when administered iv every fourth day for a total of three injections.

In addition, both compounds III and IV were evaluated in 100% DMSO against the B16F10 melanoma implanted intradermally (id) in mice (Table III). In an initial experiment, compound IV produced a T-C of 15.5 days at a daily dosage level of 20 mg/kg administered once daily for six consecutive days beginning on day 10 post-implant. In the same experiment, using the same treatment schedule, a growth delay of 11 days was obtained with compound III. In the second experiment, when the daily dose of compound IV was increased to 30 mg/kg, a more substantial growth delay of 25.5 days was achieved, whereas compound III at the same daily dose of 30 mg/kg was less active, with the T-C value obtained being 13.5 days. Thus, the aminocarbonyl component in this class of agents influences the magnitude of the antitumor effects obtained against the B16F10 melanoma.

TABLE 3

Antitumor Activity of 1,2-Bis(methylsulfonyl)-1-(2-chloroethyl)-2-(2-chloroethyl)aminocarbonylhydrazine (III) and 1,2-Bis(methylsulfonyl)-1-(2-chloroethyl)-2-methyl-aminocarbonylhydrazine (IV) Against sc B16F10 Melanoma

| Compound | Treatment Schedule, Route | Optimal Effective Dose, mg/kg/injection | T-C, Days |
|---|---|---|---|
| III | qd × 6; d.10[a]; ip | 20[b] | a)[c] 11.0 |
|  | qd × 6; d.12[a]; ip | 20[b] | b)[c] 5.5 |
|  |  | 30[b] | b)[c] 13.5 |
| IV | qd × 6; d.10[a]; ip | 10[b] | a)[c] 5.0 |
|  |  | 20[b] | a)[c] 15.5 |
|  | qd × 6; d.12[a]; ip | 20[b] | b)[c] 10.0 |
|  |  | 30[b] | b)[c] 25.5 |

[a]Day treatment initiated.
[b]Administered in 100% DMSO.
[c]Each letter (a,b) signifies a different experiment.

Summary

In summary, 2-aminocarbonyl-1,2-bis(methylsulfonyl)-1-(2-chloroethyl)hydrazines were highly active against the L1210 leukemia in mice. A representative agent of this class, compound III, was found to have substantial activity in several more stringent distal site tumor models, that unexpectedly was better than or equal to some of the best clinically active alkylating agents used for comparison in these assays. Furthermore, a comparison of compounds III and IV against the B16F10 melanoma demonstrated that the aminocarbonyl substituent influenced the degree of antineoplastic activity attainable.

It is to be understood by those skilled in the art that the foregoing description and examples are illustrative of practicing the present invention, but are in no way limiting. Variations of the detail presented herein may be made without departing from the spirit and scope of the present invention as defined by the following claims.

We claim:

1. A compound of the formula:

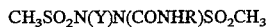

$CH_3SO_2N(Y)N(CONHR)SO_2CH_3$ where

Y is —$CH_3$ or —$CH_2CH_2Cl$; and

R is $C_1$–$C_7$ alkyl, cyclohexyl, methylcyclohexyl, —$CH_2CH=CH_2$, —$CH_2CH_2Cl$, —$CH_2CH_2CH_2Cl$, —$CH_2COOC_2H_5$, —$CH(CH_3)COOC_2H_5$ or —$CH(CH_2C_6H_5)COOC_2H_5$.

2. The compound according to claim 1 wherein Y is —$CH_2CH_2Cl$ and R is —$CH_2CH_2Cl$, —$CH_2CH=CH_2$ or —$CH_3$.

3. The compound according to claim 2 wherein R is —$CH_2CH_2Cl$ or —$CH_3$.

4. The compound according to claim 2 wherein R is —$CH_2CH_2Cl$.

5. The compound according to claim 1 wherein said $C_1$–$C_7$ alkyl is selected from the group consisting of methyl, ethyl, n-propyl, isopropyl, n-butyl, isobutyl, t-butyl, n-pentyl, isopentyl, n-hexyl, isohexyl or substituted hexyl.

6. A pharmaceutical composition for use in treating malignant tumors in mammals comprising a therapeutically effective amount of a compound of the formula:

$CH_3SO_2N(Y)N(CONHR)SO_2CH_3$ where p1 Y is —$CH_3$ or —$CH_2CH_2Cl$; and p1 R is $C_1$–$C_7$ alkyl, cyclohexyl, methylcyclohexyl, —$CH_2CH=CH_2$, —$CH_2CH_2Cl$, —$CH_2CH_2CH_2Cl$, —$CH_2COOC_2H_5$, —$CH(CH_3)COOC_2H_5$ or —$CH(CH_2C_6H_5)COOC_2H_5$.

7. The composition according to claim 6 further including a pharmaceutically acceptable excipient, additive or carrier.

8. The composition according to claim 6 wherein Y is —$CH_2CH_2Cl$ and R is —$CH_2CH_2Cl$, —$CH_2CH=CH_2$ or —$CH_3$.

9. The composition according to claim 8 wherein R is —$CH_2CH_2Cl$ or —$CH_3$.

10. The composition according to claim 9 wherein R is —$CH_2CH_2Cl$.

11. The composition according to claim 6 wherein said $C_1$–$C_7$ alkyl is selected from the group consisting of methyl, ethyl, n-propyl, isopropyl, n-butyl, isobutyl, t-butyl, n-pentyl, isopentyl, n-hexyl, isohexyl and substituted hexyl.

12. The composition according to claim 7 in intravenous dosage form.

13. The composition according to claim 7 in intramuscular dosage form.

14. The composition according to claim 7 in oral dosage form.

15. A method of treating malignant tumors in mammals comprising administering a therapeutically effective amount of a compound of the formula:

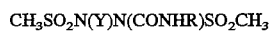

$CH_3SO_2N(Y)N(CONHR)SO_2CH_3$ where

Y is —$CH_3$ or —$CH_2CH_2Cl$; and

R is $C_1$–$C_7$ alkyl, cyclohexyl, methylcyclohexyl, —$CH_2CH=CH_2$, —$CH_2CH_2Cl$, —$CH_2CH_2CH_2Cl$, —$CH_2COOC_2H_5$, —$CH(CH_3)COOC_2H_5$ or —$CH(CH_2C_6H_5)COOC_2H_5$.

16. The method according to claim 15 wherein Y is —$CH_2CH_2Cl$.

17. The method according to claim 15 wherein said $C_1$–$C_7$ alkyl is selected from the group consisting of methyl, ethyl, n-propyl, isopropyl, n-butyl, isobutyl, t-butyl, n-pentyl, isopentyl, n-hexyl, isohexyl or substituted hexyl.

18. The method according to claim 15 wherein Y is —$CH_2CH_2Cl$ and R is —$CH_2CH_2Cl$, —$CH_2CH=CH_2$ or —$CH_3$.

19. The method according to claim 18 wherein R is —$CH_2CH_2Cl$ or —$CH_3$.

* * * * *

UNITED STATES PATENT AND TRADEMARK OFFICE
CERTIFICATE OF CORRECTION

PATENT NO. : 5,637,619
DATED : June 10, 1997
INVENTOR(S) : Alan Sartorelli, Krishnamurthy Shyam, Phillip Penkath It is certified that error appears in the above-identified patent and that said Letters Patent is hereby corrected as shown below:

Column 1, after the title insert the following:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Thirteenth Day of April, 1999

*Attest:*

Q. TODD DICKINSON

*Attesting Officer*  *Acting Commissioner of Patents and Trademarks*